(12) United States Patent
Bouchoux et al.

(10) Patent No.: US 12,390,666 B2
(45) Date of Patent: Aug. 19, 2025

(54) METHOD AND SYSTEM FOR DETECTING A CONNECTION TERMINAL

(71) Applicant: CARTHERA, Lyons (FR)

(72) Inventors: Guillaume Bouchoux, Villeurbanne (FR); Matthieu Cholvy, Peage de Roussillon (FR)

(73) Assignee: CARTHERA, Lyons (FR)

( * ) Notice: Subject to any disclaimer, the term of this patent is extended or adjusted under 35 U.S.C. 154(b) by 0 days.

(21) Appl. No.: 18/724,778

(22) PCT Filed: Dec. 28, 2022

(86) PCT No.: PCT/EP2022/087934
§ 371 (c)(1),
(2) Date: Jun. 27, 2024

(87) PCT Pub. No.: WO2023/126430
PCT Pub. Date: Jul. 6, 2023

(65) Prior Publication Data
US 2025/0128095 A1    Apr. 24, 2025

(30) Foreign Application Priority Data
Dec. 28, 2021 (FR) ...................................... 2114574

(51) Int. Cl.
A61N 7/00    (2006.01)

(52) U.S. Cl.
CPC ........ A61N 7/00 (2013.01); A61N 2007/0021 (2013.01)

(58) Field of Classification Search
None
See application file for complete search history.

(56) References Cited

U.S. PATENT DOCUMENTS 5,171,228 A    12/1992 McDonald
5,697,377 A    12/1997 Wittkampf
(Continued)

FOREIGN PATENT DOCUMENTS

EP    0485805 A2    5/1992
EP    2268218 B1    2/2016
(Continued)

OTHER PUBLICATIONS

T. L. Troy and S. N. Thennadil, "Optical properties of human skin in the near infrared wavelength range of 1000 to 2200 nm.," J. Biomed. Opt., vol. 6, No. 2, pp. 167-176, Apr. 2001.
(Continued)

Primary Examiner — Joanne M Rodden
(74) Attorney, Agent, or Firm — WOMBLE BOND DICKINSON (US) LLP

(57) ABSTRACT

The invention relates to an apparatus for treating a pathology, comprising: —an implantable device (1) including an electrical connection terminal, —a remote control unit (2) for determining and controlling operating parameters of the implantable device (1), and delivering electricity thereto, —electrical connection means for electrically connecting the implantable device (1) to the control unit (2) via the electrical connection terminal, noteworthy in that the implantable device comprises a positioning indicator in order to facilitate detection of the position of the electrical connection terminal.

19 Claims, 6 Drawing Sheets

(56) References Cited

U.S. PATENT DOCUMENTS

| | | | |
|---|---|---|---|
| 5,904,691 A | 5/1999 | Barnett et al. | |
| 2003/0187351 A1 | 10/2003 | Franck et al. | |
| 2012/0277670 A1* | 11/2012 | Goetz | A61M 25/02 |
| | | | 604/93.01 |
| 2013/0204316 A1* | 8/2013 | Carpentier | A61B 8/56 |
| | | | 607/45 |
| 2017/0340243 A1 | 11/2017 | Jain et al. | |
| 2019/0209228 A1* | 7/2019 | Canney | A61B 18/00 |
| 2020/0138580 A1 | 5/2020 | Carpentier et al. | |
| 2020/0139159 A1 | 5/2020 | Carpentier et al. | |
| 2022/0203116 A1* | 6/2022 | Park | A61N 1/08 |
| 2022/0346673 A1* | 11/2022 | Shadgan | G01N 21/359 |

FOREIGN PATENT DOCUMENTS

| | | |
|---|---|---|
| FR | 2980925 A1 | 4/2014 |
| WO | 2018007500 A1 | 1/2018 |

OTHER PUBLICATIONS

E. Salomatina, B. Jiang, J. Novak, and A. N. Yaroslavsky, "Optical properties of normal and cancerous human skin in the visible and near-infrared spectral range.," J. Biomed. Opt., vol. 11, No. 6, p. 64026, 2006.

K. P. Chan, B. Devaraj, M. Yamada, and H. Inaba, "Coherent detection techniques in optical imaging of tissues.," Phys. Med. Biol., vol. 42, No. 5, pp. 855-867, May 1997.

R. R. Alfano et al., "Time-resolved and nonlinear optical imaging for medical applications.," Ann. N. Y. Acad. Sci., vol. 838, pp. 14-28, Feb. 1998.

* cited by examiner

METHOD AND SYSTEM FOR DETECTING A CONNECTION TERMINAL

The project leading to the submission of this application has received funding from the European Union's Horizon 2020 research and innovation program under grant agreement n° 960141.

FIELD OF THE INVENTION

The present invention relates to the general technical field of treatment devices (in particular ultrasound)—for example intracorporeal or implantable devices—intended to be electrically connected to a remote control unit.

Such devices can in particular be implanted in humans and mammals to treat a pathology, such as a glioblastoma using ultrasound.

BACKGROUND OF THE INVENTION

An apparatus for treating brain conditions is known from document WO 2018/007500.

With reference to FIG. 1, such an apparatus consists of:
- an ultrasound device 1 made of non-ferromagnetic material,
- a control unit 2 remote from the ultrasound device 1, and
- means 3 for connection between the ultrasound device 1 and the control unit 2.

The ultrasound device 1 is intended to be positioned in a burr hole made in a patient's skull. It comprises:
- a support,
- one (or more) transducer(s) 12 for generating ultrasound waves for treating a brain condition,
- one (or more) electrical connection terminal(s) 13 intended to cooperate with the connection means 3.

The control unit 2 is intended to supply electrical energy to the ultrasound device 1, and to adjust its operating parameters.

The connection means 3 are intended to electrically connect the ultrasound device 1 to the control unit 2. They generally comprise:
- one (or more) electrical connection cable(s) 31, one of the ends of which is connected to the control unit, and
- one (or more) transdermal needle(s) 32 connected to the other end of the cable 31.

The principle of operation of this apparatus is as follows. Once the ultrasound device 1 is implanted in the patient's skull, a succession of treatment sessions are given thereto to treat the pathology which affects it. At each new treatment session, the ultrasound device 1 is connected to the control unit 2 via the connection means 3.

A nursing staff connects the cable 31 to the control unit 2 then inserts the needle 32 through the patient's skin to the terminal 13 of the ultrasound device.

Once the end of the needle 32 connected to the terminal 13, the control unit 2 can be activated to supply the ultrasound device 1 with electrical energy.

Currently, the terminal 13 of the ultrasound device 1 is detected by palpation through the patient's scalp, because the latter has been sutured in place by the surgeon after implantation.

However, in certain patients, the detection of the terminal 13 may prove to be difficult due to various factors (edema, significant thickness of the scalp, etc.). This increases the time required to electrically connect the needle 32 to the terminal 13c (time longer than two minutes). Furthermore, multiple insertion attempts may be necessary, increasing discomfort for the patient.

A purpose of the present invention is to propose a method and a system allowing healthcare personnel to facilitate the detection of the position of a connection terminal of an implanted ultrasound device.

BRIEF DESCRIPTION OF THE INVENTION

To this end, the invention proposes an apparatus for treating a pathology comprising:
- a device implantable at an opening made in the cranium of a patient, the implantable device including a treatment unit having upper and lower faces and including an electrical connection terminal extending on the upper face,
- a remote control unit for determining and controlling operating parameters of the implantable device, and delivering electricity thereto,
- electrical connection means for electrically connecting the treatment unit to the remote control unit via the electrical connection terminal, noteworthy in that the implantable device comprises a positioning indicator in order to facilitate detection of the position of the electrical connection terminal, said positioning indicator comprising at least two light sources, such as light-emitting diodes, each capable of emitting light radiation towards the outside of the upper face, the electrical connection terminal extending between said light-emitting diodes.

Preferred but non-limiting aspects of the present invention are the following:
- the wavelength of the light radiation emitted by each light-emitting diode can be comprised between 600 and 1600 nanometers, preferably comprised between 850 and 1250 nanometers, and even more preferably comprised between 950 and 1100 nanometers, in particular of the order of 1050 nanometers;
- the distance between the light-emitting diodes can be comprised between 15 and 60 millimeters, preferably comprised between 20 and 40 millimeters, in particular of the order of 25 millimeters;
- the distance between each light-emitting diode and the connection terminal can be comprised between 9 and 35 millimeters, preferably comprised between 12 and 25 millimeters, in particular of the order of 15 millimeters;
- each light-emitting diode can be configured to emit light radiation having a respective wavelength different from the wavelengths of the other light-emitting diodes;
- each light-emitting diode can be configured to emit light radiation having a respective intensity different from the intensities of the other light-emitting diodes;
- the positioning indicator may further comprise at least one resonant passive electrical circuit;
- said and at least one resonant passive electrical circuit can be configured to interact with a resonant active electrical circuit integrated into a location unit, said interaction allowing to supply the implantable medical device with electrical energy by induction;
- said and at least one resonant passive electrical circuit may comprise a coil functionally coupled to a capacitor, said coil extending around the electrical connection terminal;
- said and at least one resonant passive electric circuit can be configured so that the resonance frequency of said and at least one resonant passive electric circuit is comprised between 10 MHz and 50 MHZ;

the implantable device may comprise:
- a support plate including first and second opposite faces, the treatment unit being intended to be mounted on the first face of the support plate,
- a fixing part intended to be positioned on the second face of the support plate and being configured to press the treatment unit against the first face of the support plate when the treatment unit, the support plate and the fixing part are assembled, the fixing part including the positioning indicator;

advantageously:
- the support plate may comprise a through orifice,
- the electrical connection terminal may comprise a pin projecting outwards from the treatment unit, the pin being intended to be positioned in the through orifice of the support plate,
- the fixing part may comprise:
  - a conduit adapted to receive at least a portion of the pin, and
  - a peripheral flange extending perpendicular to a longitudinal axis of the conduit, the flange being intended to be positioned on the second face of the support plate, the peripheral flange including the positioning indicator.

BRIEF DESCRIPTION OF THE DRAWINGS

Other advantages and characteristics of the method and the system according to the invention will become clearer from the description which follows of several variants of execution, given by way of non-limiting examples, from the appended drawings in which.

DETAILED DESCRIPTION OF THE INVENTION

Different examples of the system and the method according to the invention will now be described with reference to the figures. In these different figures, the equivalent elements are designated by the same numerical reference.

1. Generalities

Figure 2:
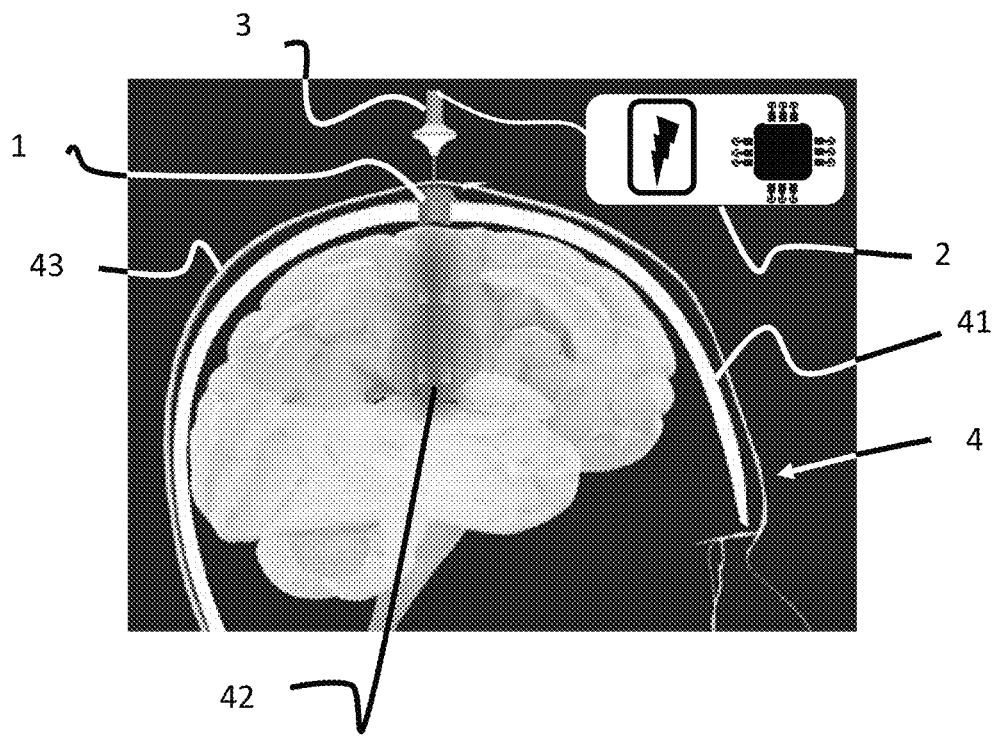
FIG. 2 is a schematic sectional representation of a treatment apparatus according to the invention.

With reference to FIG. 2, the treatment apparatus comprises:
- a medical device 1 implantable in a patient 4,
- a remote control unit 2 for determining and controlling operating parameters of the implantable device 1, and delivering electricity thereto,
- electrical connection means 3 for electrically connecting the implantable device 1 to the remote control unit 2,
- a unit for locating the implantable device 1.

The medical device 1 is capable of being implanted in a cranial bone 41 of the patient 4 to allow the treatment and/or imaging of a brain area of interest 42. For this purpose, the practitioner performs a craniectomy. An incision is made in the scalp 43, then the skin (and muscles if applicable) is lifted (are lifted) to expose the skull 41. The skull 41 is then cut to form a bone flap. The cranial bone flap is removed to make way for a cranial opening in which the implantable medical device 1 can be positioned. Once the implantable medical device 1 is correctly positioned, it is fixed on the periphery of the cranial opening by any means known to the person skilled in the art (anchoring screw, bonding, etc.), then the scalp 43 (skin and muscles) is put back in place to cover the implantable medical device 1.

At each new treatment/imaging session, a nursing staff electrically connects the implantable medical device 1 to the remote control unit 2 using the connection means 3.

Figure 1:
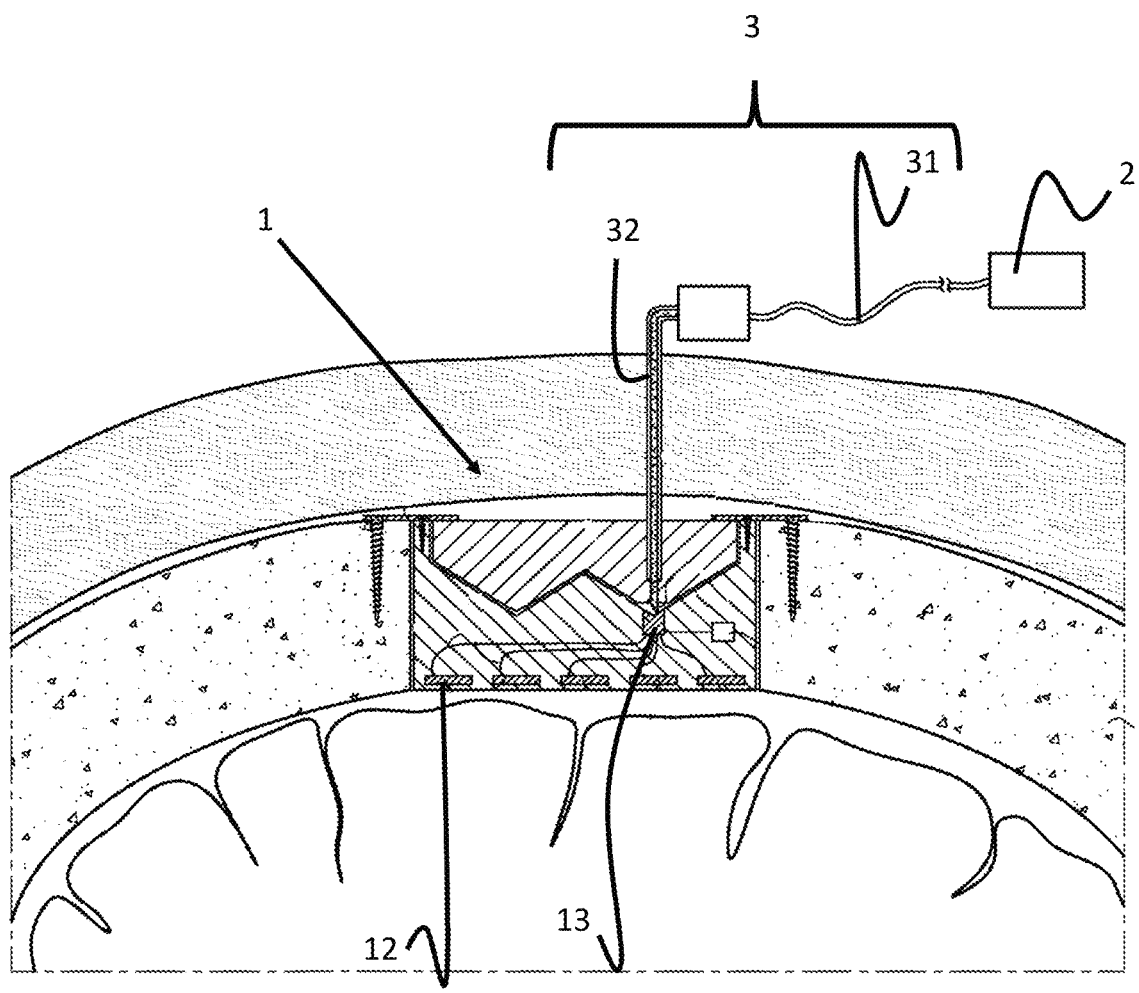
FIG. 1 schematically illustrates an example of an apparatus for treating a brain condition including an ultrasound device electrically connected to a remote control unit using connection means (transdermal needle+cable)

As illustrated in FIG. 1, these connection means 3 comprise in particular:
- an electrically conductive cable 31,
- a needle 32 mounted at one of the ends of the cable 31, the needle 32 being able to be introduced into a connection terminal 113 of the ultrasound unit 11, and
- a connection socket (not shown) at the other end of the cable 31, the connection socket being able to be connected to a complementary socket of the control unit 2.

More precisely, the nursing staff connects the connection socket to the remote control unit 2. The nursing staff then inserts the needle 32 into the scalp 43 of the patient 4, and introduces the end of the needle into a connection terminal 113 (illustrated in FIG. 3) so as to finalize the electrical connection of the implantable medical device 1 to the remote control unit 2.

It may be difficult for the nursing staff to identify by palpation the position of the connection terminal 113 once the medical device 1 has been implanted, the latter being covered by the scalp 43 (few and muscles) of the skull of the patient 4. However, knowledge of the precise position of the connection terminal 113 is necessary to ensure adequate positioning of the transdermal needle 32.

To facilitate detection of the connection terminal 113 through the scalp 43 of the patient 4, the implantable medical device 1 comprises a positioning indicator. This positioning indicator is configured to interact with the location unit. This location unit allows to detect the precise position of the connection terminal 113.

Advantageously, the location unit can be contained in a handpiece, or be integrated into the connection means 3.

2. Implantable Medical Device 2.1. General Presentation

Figure 3:
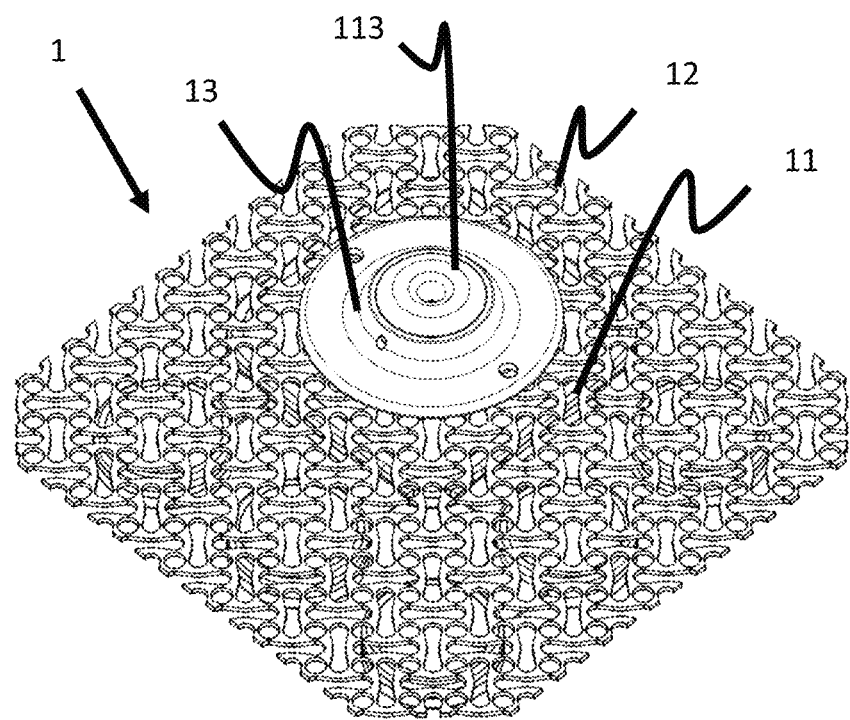
FIG. 3 is a schematic perspective representation of an implantable medical device.

With reference to FIG. 3, the implantable medical device 1 comprises:
- an ultrasound unit 11 for emitting ultrasound waves for imaging or treatment, a support plate 12 on which the ultrasound unit 11 is mounted, and a fixing part 13 for blocking the ultrasound unit 11 against the support plate 12.

The ultrasound unit 11, the support plate 12, and the fixing part 13 are distinct elements intended to be assembled to form the implantable medical device 1. More precisely to form the implantable medical device 1, these different elements are assembled so that the support plate 12 extends between the ultrasound unit 11 and the fixing part 13.

When the implantable medical device 1 is positioned in the cranial opening, the ultrasound unit 11 extends facing the brain area of interest 42. Thus, once implanted, the ultrasound unit 11 faces the brain area of interest 42, while the fixing part 13 extends facing the scalp 43 of the patient 4.

The positioning indicator makes it easier to detect the position of the connection terminal 113 by the nursing staff in order to facilitate the insertion of the needle 32 into said connection terminal 113.

For this purpose, the positioning indicator comprises one (or more) marker(s) surrounding the connection terminal 113. This (or these) marker(s) can be of the optical marker type and/or electromagnetic resonance marker, as it will be described in more detail later.

The use of a positioning indicator allows to reduce the time necessary for the implementation of an imaging and/or treatment session of the brain area 42, in particular compared to a solution based on the use of a neuro-navigation set.

Indeed, to use a neuro-navigation set, it may be necessary to move the patient 4, which:

is time consuming, increases the risk of infection, and can cause additional stress for the patient.

2.2. Ultrasound Unit

Figure 4:
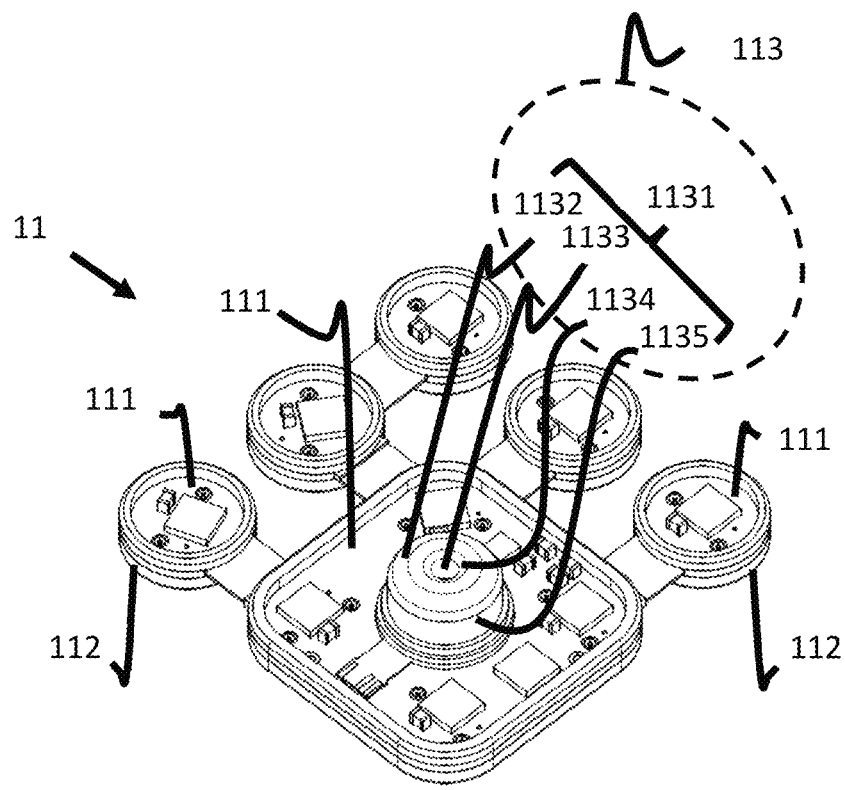
FIG. 4 is a schematic representation of an ultrasound unit of the implantable medical device.

With reference to FIG. 4, the ultrasound unit 11 comprises:

one (or more) electronic card(s) 111 adapted to exchange electrical power and control signals with the remote control unit 2, one (or more) ultrasonic transducer(s) 112—for example circular transducer(s) of 10 millimeters in diameter (each)—adapted to generate ultrasound waves for treatment (or imaging) of the area brain of interest 42, and an electrical connection terminal 113 for connecting the ultrasound unit 11 to the remote control unit 2.

The electronic card(s) 111 and the transducer(s) 112 are positioned on a first face of the support plate 12 when the implantable medical device 1 is assembled. The electronic card 111 and the transducers 112 being known to the person skilled in the art, they will not be described in more detail below.

The electrical connection terminal 113 allows to connect the implantable medical device 1 to the external control unit 2 which supplies the transducers 112 with electrical energy, and adjusts their operating parameters.

The connection terminal 113 comprises a pin 1131 projecting outwards from an upper face of the ultrasound unit 11. The upper wall 1132 of the pin 1131 includes a blind hole 1133 in which the end of the needle 32 is intended to be introduced to electrically connect the ultrasound unit 11 to the electrical connection means 3. Advantageously, the connection terminal 113 may comprise a conical flare (or countersink) 1134 provided at the entrance to the blind hole 1133. This allows the needle 32 to be guided towards the blind hole 1133 to facilitate the introduction of the end of the needle into the blind hole 1133.

The side wall of the pin 1131 may comprise a threading 1135. This threading 1135 is intended to cooperate by screwing with a corresponding threading provided on the internal face of a conduit of the fixing part 13. This allows to ensure the securing of the ultrasound unit 11, the support plate 12 and the fixing part 13 during the assembly of the medical device 1. The fact that the ultrasound unit 11 cooperates by screwing with the fixing part 13 allows, during the phase of connecting the intracranial device to the control unit, to distribute the force applied by the needle on the connection terminal to an entire surface of the support plate 12.

2.3. Support Plate

Figure 5:
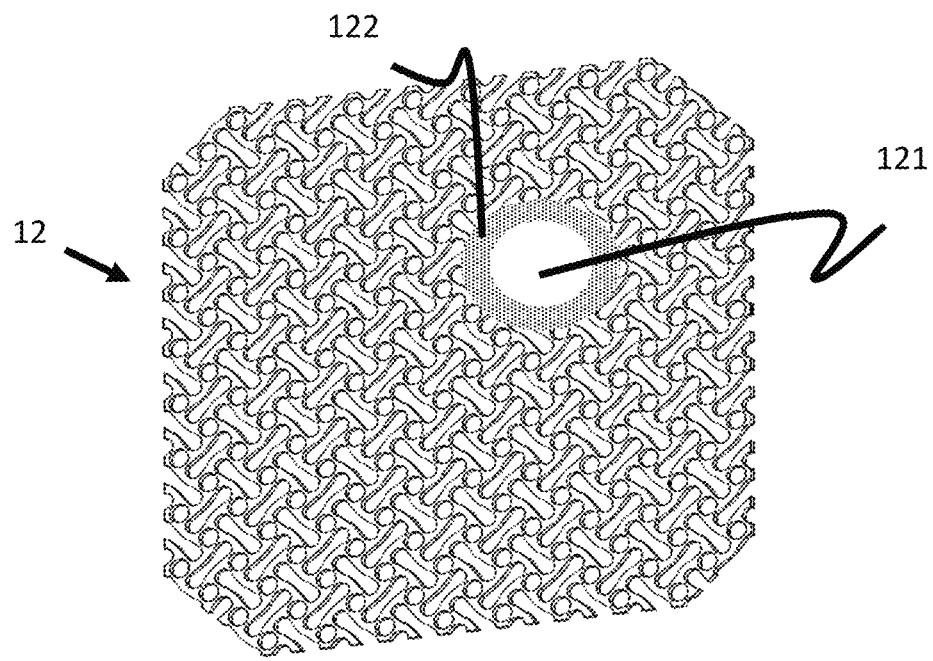
FIG. 5 is a schematic representation of a support plate of the implantable medical device.

An example of support plate 12 is illustrated with reference to FIG. 5. The support plate 12 is generally rectangular, but can have any shape, such as a circular, triangular or square shape.

The material constituting the support plate 12 can be a metal, such as titanium or any other metal known to the person skilled in the art (possibly covered with parylene or the like if the metal used is not biocompatible in itself).

The support plate 12 comprises a through orifice 121 for the passage of the connection terminal 113. The edge 122 of the through orifice 121 can be covered with a layer of polymer material, such as silicone. This layer of polymer material allows to limit the risk of loosening between the connection terminal 113 and the fixing part 13.

2.4. Fixing Part

Figure 6:
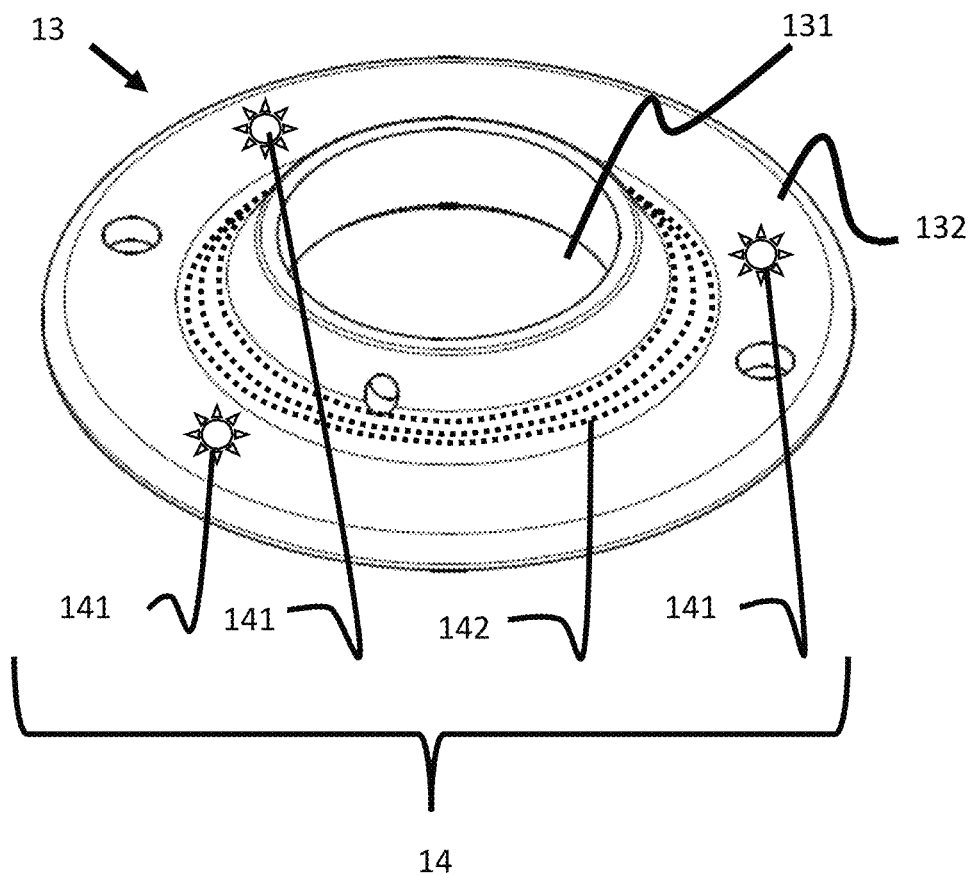
FIG. 6 is a schematic perspective representation of a fixing part of the implantable medical device.

With reference to FIG. 6, the fixing part 13 comprises:

a conduit 131 capable of receiving the pin 1131, and a peripheral flange 132.

The conduit 131 is intended to cooperate with the connection terminal 113 so as to block the support plate 12 between the ultrasound unit 11 and the fixing part 13. More precisely, the conduit 131 consists of a nut the tapped hole of which is intended to cooperate by screwing with the threading 1135 of the side wall of the pin 1131. In other words, the internal face of the conduit 131 comprises a thread complementary to the threading 1135 of the side wall of the pin 1131.

The flange 132 extends at the base of the conduit 131, perpendicular to the axis of revolution of the conduit 131. It is intended to come into contact with a second face of the support plate 12 opposite the first face opposite the upper face of the ultrasound unit 11. The flange 132 allows to press the support plate 12 against the ultrasound unit 11 when the implantable medical device 1 is assembled.

Preferably, the flange 132 is circular in shape. This allows better distribution of the force applied by the needle when introducing it into the blind hole 1143 of the connection terminal 114.

The principle of assembling the implantable device 1 is as follows. An operator inserts the pin 1131 of the connection terminal 113 through the through orifice 122 of the support plate 12. Once the ultrasound unit 11 in position on the first face of the support plate 12, the operator then places the fixing part 13 on the connection terminal 113. The fixing part 13 is installed on the pin 1141 so that the base of the conduit 131 (at which the flange 132 extends) faces the second face of the support plate 12 (opposite to the first face). The operator then screws the fixing part 13 onto the pin 1131, which causes the flange 132 to be pressed against the support plate 12: the ultrasound unit 11, the support plate 12 and the fixing part are then integral. Thus the implantable medical device 1 illustrated in FIG. 2 is obtained.

Advantageously, and as illustrated in FIG. 6, the flange 132 may comprise the positioning indicator making it easier to detect the connection terminal 113 by the medical personnel. The fact that the positioning indicator is integrated into the fixing part 13 allows to limit the modifications to be made to the device described in WO 2018/007500 to facilitate the detection of the connection terminal 113.

Various characteristics associated with the positioning indicator according to the invention will now be described in more detail.

2.5. Positioning Indicator

Different solutions have been proposed for the positioning indicator, including:
- an optical solution in which the positioning indicator comprises two (or more than two) light sources—such as light-emitting diodes (LED)—surrounding the connection terminal, and/or
- an electromagnetic solution in which the positioning indicator comprises one (or more) resonant passive electrical circuit(s) surrounding the connection terminal.

In all cases, the location unit comprises one (or more) sensor(s) adapted to interact with the positioning indicator. This (or these) sensor(s) may consist of:
- a light detector—such as a camera—when the positioning indicator comprises optical markers, and/or
- a resonant circuit when the positioning indicator comprises one (or more) resonant active electrical circuit(s).

The advantages associated with each of the (optical/electromagnetic) solutions considered for the positioning indicator will now be presented with reference to the figures.

2.5.1. Optical Solution 2.5.1.1. Principle

The optical solution uses the detection of light radiation emitted by light sources (such as LEDs) through the patient's scalp to detect the position of the connection terminal.

One (or more) light detector(s)—such as one (or more) camera(s)—is (are) located in the location unit (which may or may not be integrated into the connection means) and receives (receive) the light emitted by the light sources.

Figure 7:
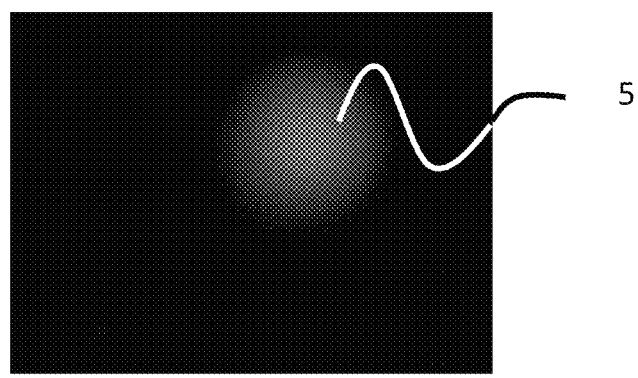
FIG. 7 is an image representing light radiation emitted through a phantom simulating the behavior of a scalp.

Due to diffusion through the tissues of the scalp, the light radiation emitted by each LED light source appears as a "spot" 5 on the detector(s), as illustrated in FIG. 7.

The center of each spot 5 corresponds to the position of the light source having generated the light radiation associated with said spot.

To determine the position of the connection terminal 113 in the case of a positioning indicator including three light sources each located at an equal distance from said connection terminal 113, the principle is as follows.

Figure 8:
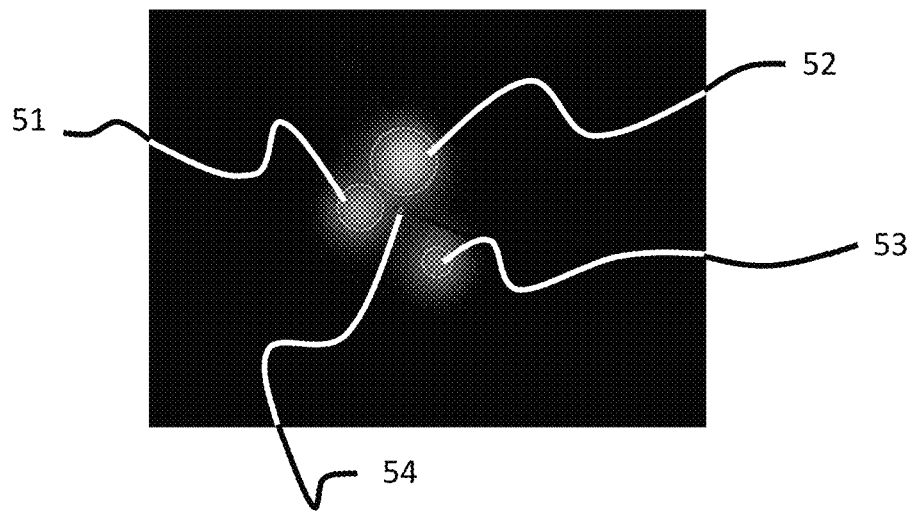
FIG. 8 is an image of three light rays emitted through the phantom simulating the behavior of the scalp.

An operator moves the location unit over the patient's scalp. The detector(s) acquire(s) one (or more) image(s) of the light radiation emitted by the light sources. This (or these) images can be displayed on display means such as a screen. Such an image is shown in FIG. 8.

The center of each spot 51, 52, 53 is calculated—by a calculator which can be integrated (or not) into the location unit—to estimate the position of each light source. Indeed, as indicated previously, the center of each spot is representative of the position of the light source that produced the spot. The centers thus calculated can be displayed on the image (or images) displayed on the display means.

The barycenter 54 of the centers of the spots 51-53 is then calculated by the calculator to estimate the position of the connection terminal. More precisely, the barycenter of the centers of the spots 51-53 is representative of the position of the connection terminal 113.

The fact of using 3 LEDs, each making large and separable spots, allows for much greater precision than the resolution of each spot.

While monitoring the camera, the operator moves the needle from the connection means to the center of the connection terminal, and introduces it into the patient's scalp to electrically connect the medical device 1 to the control unit 2.

2.5.1.2. Experimentation and Results

An experiment was carried out to study:
- the influence of scalp thickness, and
- the effect of the wavelength of light radiation emitted by each light source.

For this experiment, a light-emitting diode was inserted into an agar phantom mimicking the optical behavior of the scalp. This agar phantom was composed of:
- one liter of water,
- 20 g of powdered gelose,
- 1.67 g of titanium dioxide ($TiO_2$),
- 0.19 ml of Indian ink, and
- 1 g of benzoic acid.

A PiNoIR Raspberry Pi camera (emulating the behavior of the location unit) was used to capture the light passing through the agar phantom. The results of this experiment are shown in FIG. 9 which plots spot diameter at 50% luminous intensity as a function of agar phantom thickness for light emitting diodes (LEDs) of different wavelengths.

Figure 9:
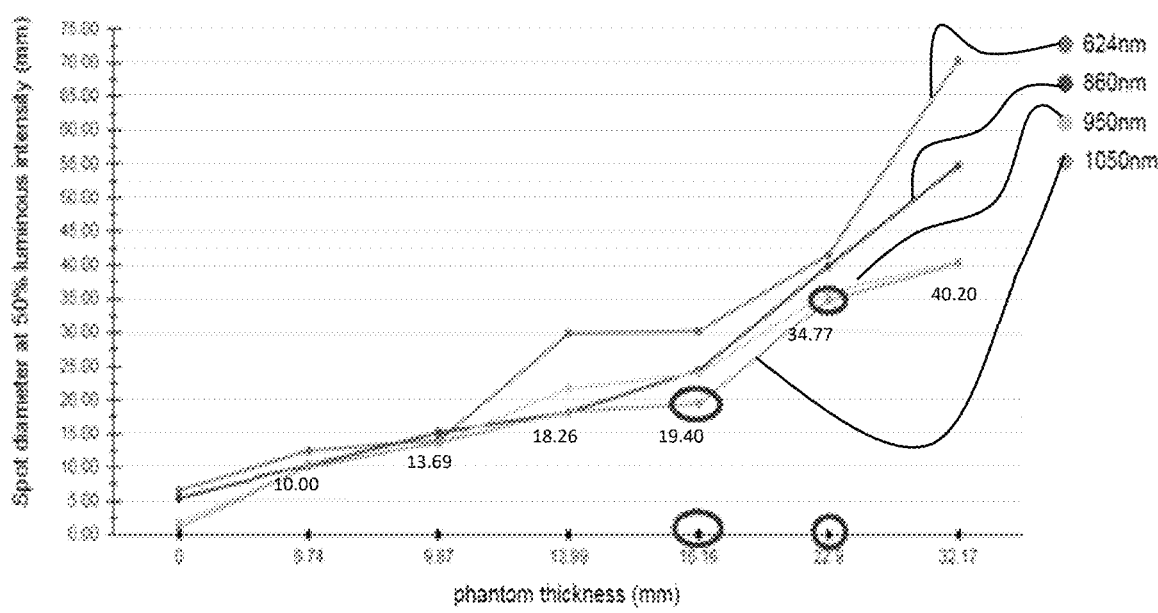
FIG. 9 is a curve illustrating the luminous intensity of radiation emitted through the phantom simulating the behavior of the scalp as a function of the thickness of said phantom.

As the reader will appreciate in FIG. 9, the diameter of the spot increases with the thickness of the phantom, suggesting a decrease in the positional precision of the LED-type light source.

The combination of a light-emitting diode (LED) emitting light radiation at a wavelength of 1050 nm and a phantom of thickness 16.16 mm gives a spot of sufficiently small diameter (19.40 mm) to distinguish three spots in the case of an implantable medical device 1 including three light-emitting diodes distributed at an equal distance from the connection terminal 113 and separated from each other by a distance of 25 millimeters).

For information purposes, tests were carried out with an implantable medical device 1 including a positioning indicator including three light-emitting diodes (LED):
- emitting light radiation at a wavelength of 1050 nm (infrared),
- separated from each other by a distance of 25 millimeters,
- distributed at an equal distance from the connection terminal.

The location unit allowed to locate the position of connection terminal 113:
- with an accuracy of 2.4 mm in 87% of cases, and
- with an accuracy of 3.2 mm in 100% of cases, for 30 tests carried out with two planar phantoms with thicknesses of 9 mm and 14 mm and a non-planar phantom having a variable thickness comprised between 6 mm and 13 mm.

Of course, the reader will appreciate that light sources emitting light radiation at longer wavelengths can be used to minimize the phenomenon of diffusion through the patient's scalp.

Furthermore, the reader will appreciate that light sources emitting light radiation at wavelengths different from each other can be used in the positioning indicator. This allows to detect the center of each spot (and therefore the position of each light source), even in the event of superposition of spots produced by different light sources.

2.5.2. Electromagnetic Resonance Solution

To detect the position of the connection terminal 113, the electromagnetic solution uses an impedance variation when two resonant circuits interfere.

For the implementation of the electromagnetic solution, several resonant electrical circuits are disposed in the location unit and in the implantable medical device 1.

More precisely:
- the positioning indicator of the implantable medical device comprises:
  - a resonant passive electrical circuit including a coil surrounding the connection terminal 113, or
  - several resonant passive electrical circuits each including one (or more) respective coil(s), said coils being distributed around the connection terminal 113 at an equal distance therefrom,
- the location unit comprises one (or more) resonant active electrical circuit(s) each including one (or more) coil(s) disposed (distributed) on a surface intended to come into contact with the scalp of the patient.

The fact that the positioning indicator comprises a resonant electrical circuit including a coil—rather than a permanent magnet—allows to make the treatment apparatus according to the invention compatible with magnetic resonance imaging (MRI) techniques.

If the optical solution allows to detect the position of the connection terminal with great precision (±1.6 mm), the electromagnetic solution provides information concerning the orientation of the connection terminal, which facilitates again the operator's gesture to insert the end of the transdermal needle 32 into the connection terminal 113.

2.5.2.1. Principle

The electromagnetic solution uses impedance variation when two resonant circuits are close enough to interfere, or when the impedance of a circuit including a coil is changed by the presence of a metal or magnet.

The principle of the electromagnetic solution is to use the variation caused by the electromagnetic induction when moving the location unit above the implantable medical device to locate the position of the connection terminal 113.

More precisely, a primary coil (contained in the location unit) induces an electromagnetic field directed towards a secondary coil (contained in the implantable medical device). When the primary and secondary coils are brought together, the transmission of power to the secondary coil causes a loss in the resonant electrical circuit including the primary coil. By detecting the corresponding variation in the primary circuit, the location of the connection terminal can be deduced.

The principle of the electromagnetic solution is well known and has been described in numerous documents, such as U.S. Pat. No. 5,697,377.

2.5.2.2. Experimentation and Results

An experiment was carried out to study the accuracy in detecting the connection terminal using the electromagnetic solution.

The implantable medical device comprised a resonant electrical circuit including:
- a 5-turn coil having a diameter of 2.5 cm integrated into the flange 132 of the fixing part 13,
- a capacitance mounted in parallel whose value was chosen to obtain a resonant circuit having a resonance frequency of 16.5 MHz.

This implantable medical device was inserted into an agar phantom mimicking the behavior of the scalp. This agar phantom was composed of:
- 80 cl of water,
- 20 g of glycine,
- 0.6 g of sodium chloride (NaCl), and
- of 1.6 g of gelose powder.

Two types of location units were tested:
- the first location unit comprised a coil identical to that contained in the resonant circuit of the implantable medical device and a capacitor connected in parallel and whose value was chosen to obtain a resonant circuit having a resonance frequency of 16.5 MHZ (resonance frequency identical to the resonance frequency of the resonant circuit contained in the implantable medical device),
- the second location unit comprised a spiral coil (interesting shape for energy transmission) of 18 turns and an external diameter approximately equal to 3 cm, and a capacitance adjusted to have a resonance frequency equal to 16.5 MHZ (resonance frequency of the resonant circuit contained in the implantable medical device).

The fact that the coils (contained in the implantable medical device and in the location unit) are respectively associated with capacitances allowed to obtain resonant circuits at the same frequency in the medical device on the one hand and in the location unit on the other hand.

The inventors have in fact discovered that the use of resonant circuits allowed:
- to improve the efficiency of the coupling between the medical device and the location unit, and
- to improve the detection capacity of this coupling, compared to solutions based on the use of a coil and a magnet for example.

The accuracy in detecting the position of the connection terminal was lower than that obtained with the optical solution.

However, the inventors discovered that the combination of the two solutions allowed to facilitate the connection of the transdermal needle to the connection terminal 113, in particular by providing precise information on the position of the connection terminal (optical solution) and on its orientation (electromagnetic solution).

Furthermore, the use of resonant circuits as proposed with the electromagnetic solution allows to electrically supply the implantable medical device by induction. It is therefore no longer necessary for batteries to be integrated into it for the implementation of the optical solution.

3. Location Unit

As indicated previously, the location unit can be integrated into the connection means or be separated therefrom. In particular, the location unit can be integrated:
- into the connection means, or
- into a tool intended to be fixed on the connection means, or
- into an intermediate tool completely independent of the connection means and allowing the operator to locate the implant.

In a variant embodiment, the location unit is integrated into a tool including a pre-emption handle and the location unit including proximity sensors capable of interfering with the positioning indicator contained in the implantable medical device.

The proximity sensors evaluate the alignment of the handle with the medical device, in order to detect the position of the connection terminal and thus facilitate the insertion of the transdermal needle therein.

In operation, the operator can mark the needle insertion location on the skin with a felt-tip pen, then remove the intermediate tool and puncture the skin at the mark.

4. Example of Implementation

Figure 10:
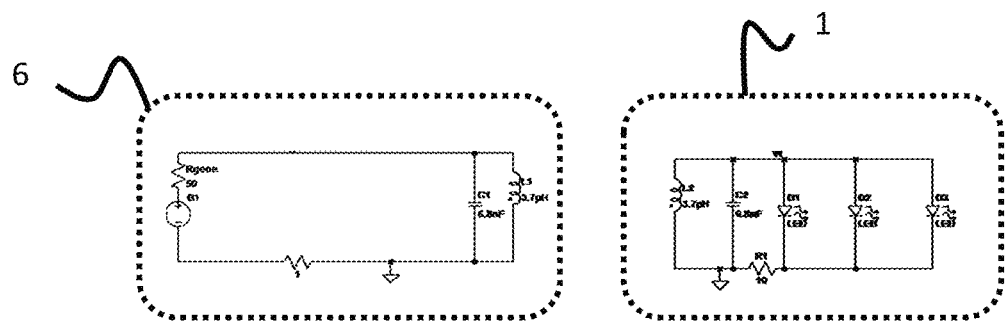
FIG. 10 is a schematic representation of electronic circuits integrated into a location unit on the one hand and into the implantable medical device (and more precisely into a flange of the implantable medical device).

With reference to FIG. 10, an example of implementation of the treatment apparatus is illustrated. More precisely, examples of electronic circuits integrated into the medical device 1 on the one hand, and into the location unit 6 on the other hand were illustrated.

The medical device comprises an LC resonant circuit (including a 3.7 µH coil L2 mounted in parallel with a 6.8 nF capacitance C2), and three LED type light sources D1, D2, D3 each mounted in parallel with the LC resonant circuit. This electronic circuit is integrated in the fixing part, in particular in the flange.

The location unit 6 comprises a camera (not shown), a generator B, a resistor $R_{gene}$ mounted in series with the generator B, and an LC resonant circuit (including a 3.7 µH coil L1 connected in parallel with a 6.8 nF capacitance C1) connected to the generator B.

5. Principle of Operation

The principle of operation of the treatment apparatus described above is as follows.

At each new treatment session, an operator moves the location unit close to the patient's head.

For better detection or to limit the energy to be supplied to the resonant circuit, it is possible to slide the location unit over the patient's scalp. Indeed, to supply electrical energy to the light sources by induction, it is preferable to limit the distance between the resonant circuit of the location unit and the resonant circuit contained in the medical device.

To avoid contamination, the location unit can be covered with a sterile envelope, such as an "Ultrasound Probe Cover" type envelope developed by the company CIVCO.

The location unit is moved over the patient's head. When a maximum impedance disturbance is detected at the location unit, it emits a signal (visual or audible, etc.) to alert the operator of the position of the connection terminal. The electromagnetic energy transmitted by the resonant circuit of the location unit allows to power supply the light sources of the positioning indicator by induction.

The detector of the location unit acquires an image of the light spots produced by the light sources contained in the medical device. The location unit calculator calculates the centers of the spots (representative of the positions of the light sources), and estimates the position of the barycenter of the centers of the spots (representative of the position of the connection terminal). This different information can be displayed on the display means.

The operator can then take a marker (such as a felt-tip pen) and mark the position of the barycenter which corresponds to the position of the point to be pricked with the transdermal needle.

The reader will have understood that numerous modifications can be made to the treatment apparatus described above without departing from the teachings presented here.

For example, even if the apparatus was presented with reference to an implantable medical device allowing the treatment and/or imaging of a brain area of interest by ultrasound, it is obvious that:

The implantable medical device can be configured for the treatment and/or imaging of another tissue of interest in the human or animal body, The implantable medical device may comprise a treatment unit based on a technology other than ultrasound.

Furthermore, the various components allowing the implementation of the optical and electromagnetic solutions presented above can be reversed in the implantable medical device and in the location unit. In particular, the implantable medical device can integrate a camera and a resonant active electrical circuit, while the location unit integrates light sources and a resonant passive circuit.

The invention claimed is:

1. An apparatus for treating a pathology comprising: an implantable device implantable configured to be implanted at an opening made in a cranium of a patient, wherein said implantable-device includes an ultrasound treatment unit having which has upper and lower faces and including an electrical connection terminal extending which extends on the upper face, a remote-control configured to determine and control operating parameters of the implantable device, and delivering to deliver electricity thereto to the implantable device, electrical connectors configured to electrically connect the ultrasound treatment unit to the remote-control via the electrical connection terminal, wherein the implantable device comprises a positioning indicator in order to facilitate detection of the position of the electrical connection terminal, wherein said positioning indicator comprises at least two light-emitting sources configured to emit light radiation towards the outside of the upper face, and wherein the electrical connection terminal extends between said light-emitting sources.

2. The apparatus according to claim 1, wherein the wavelength of the light radiation emitted by each light-emitting source is comprised between 600 and 1600 nanometers.

3. The apparatus according to claim 1, wherein the distance between the light-emitting sources is comprised between 15 and 60 millimeters.

4. The apparatus according to claim 1, wherein the distance between each light-emitting source and the connection terminal is comprised between 9 and 35 millimeters.

5. The apparatus according to claim 1, wherein each light-emitting source is configured to emit light radiation having a respective wavelength different from the wavelengths of the other light-emitting sources.

6. The apparatus according to claim 1, wherein each light-emitting source is configured to emit light radiation having a respective intensity different from the intensities of the other light-emitting sources.

7. The apparatus according to claim 1, wherein the positioning indicator further comprises at least one resonant passive electrical circuit.

8. The apparatus according to claim 7, wherein said at least one resonant passive electrical circuit is configured to interact with a resonant active electrical circuit integrated into a location unit, and wherein said interaction allows to supply the implantable medical device with electrical energy by induction.

9. The apparatus according to claim 8, wherein said at least one resonant passive electrical circuit comprises a coil functionally coupled to a capacitor, and wherein said coil extends around the electrical connection terminal.

10. The apparatus according to claim 7, wherein said at least one resonant passive electric circuit is configured so that the resonance frequency of said at least one resonant passive electric circuit is comprised between 10 MHz and 50 MHz.

11. The apparatus according to claim 1, wherein the implantable device comprises:

a support plate including first and second opposite faces, wherein the ultrasound treatment unit is configured to be mounted on the first face of the support plate, a fixing part configured to be positioned on the second face of the support plate and configured to press the ultrasound treatment unit against the first face of the support plate when the ultrasound treatment unit, the support plate and the fixing part are assembled, and wherein said fixing part includes the positioning indicator.

12. The apparatus according to claim 11, wherein:

the support plate comprises a through orifice, the electrical connection terminal comprises a pin which projects outwards from the ultrasound treatment unit, and which is configured to be positioned in the through orifice of the support plate, the fixing part comprises:

a conduit adapted to receive at least a portion of the pin, and a peripheral flange which extends perpendicular to a longitudinal axis of the conduit and which is configured to be positioned on the second face of the support plate, and wherein said peripheral flange includes the positioning indicator.

13. The apparatus according to claim 2, wherein the wavelength of the light radiation emitted by each light-emitting source is comprised between 850 and 1250 nanometers.

14. The apparatus according to claim 13, wherein the wavelength of the light radiation emitted by each light-emitting source is comprised between 950 and 1100 nanometers.

15. The apparatus according to claim 14, wherein the wavelength of the light radiation emitted by each light-emitting source is of 1050 nanometers.

16. The apparatus according to claim 3, wherein the distance between the light-emitting sources is comprised between 20 and 40 millimeters.

17. The apparatus according to claim 16, wherein the distance between the light-emitting sources is of 25 millimeters.

18. The apparatus according to claim 4, wherein the distance between each light-emitting source and the connection terminal is comprised between 12 and 25 millimeters.

19. The apparatus according to claim 18, wherein the distance between each light-emitting source and the connection terminal is of 15 millimeters.

* * * * *